United States Patent [19]
Miller et al.

[11] Patent Number: 5,756,073
[45] Date of Patent: May 26, 1998

[54] STRIPED DENTIFRICE STABLE TO COLOR BLEEDING

[75] Inventors: Jeffrey M. Miller; Mike Wong, both of Middlesex; Michael Prencipe, Mercer; Richard J. Crawford, Hunterdon, all of N.J.

[73] Assignee: Colgate Palmolive Company, New York, N.Y.

[21] Appl. No.: 747,690

[22] Filed: Nov. 12, 1996

[51] Int. Cl.$^6$ .................... A61K 7/16; A61K 7/20; A61K 9/50
[52] U.S. Cl. .................... 424/49; 414/52; 414/53
[58] Field of Search .......................... 424/49–58

[56] References Cited

U.S. PATENT DOCUMENTS

| | | | |
|---|---|---|---|
| 3,070,510 | 12/1962 | Cooley et al. | 165/93 |
| 3,151,027 | 9/1964 | Cooley et al. | 167/93 |
| 3,325,368 | 6/1967 | Wood | 167/93 |
| 3,516,941 | 6/1970 | Matson . | |
| 3,928,559 | 12/1975 | Patino et al. . | |
| 3,929,988 | 12/1975 | Barth . | |
| 3,945,980 | 3/1976 | Tsubakimoto et al. | 260/39 |
| 3,957,964 | 5/1976 | Grimm, III . | |
| 4,007,259 | 2/1977 | Patino et al. . | |
| 4,069,176 | 1/1978 | Tsubakimoto et al. | 260/390 |
| 4,071,614 | 1/1978 | Grimm, III . | |
| 4,129,638 | 12/1978 | Ritze . | |
| 4,201,404 | 5/1980 | Charbonneau et al. . | |
| 4,202,878 | 5/1980 | Ritze . | |
| 4,348,378 | 9/1982 | Kosti . | |
| 4,487,757 | 12/1984 | Kiozpeoplou | 424/49 |
| 4,533,484 | 8/1985 | Walles et al. | 252/117 |
| 4,769,079 | 9/1988 | Clark et al. | 106/402 |
| 4,769,080 | 9/1988 | Clark et al. | 106/402 |
| 4,773,936 | 9/1988 | Clark et al. | 106/402 |
| 4,814,160 | 3/1989 | Carter et al. | 424/49 |
| 4,840,676 | 6/1989 | Clark et al. | 166/462 |
| 5,020,694 | 6/1991 | Pettengill | 222/145 |
| 5,038,963 | 8/1991 | Pettengill et al. | 222/145 |
| 5,149,521 | 9/1992 | Hirose et al. | 424/58 |
| 5,206,010 | 4/1993 | Inoue et al. | 424/49 |
| 5,411,802 | 5/1995 | Kumar et al. | 428/402 |
| 5,460,805 | 10/1995 | Davis et al. | 424/67 |
| 5,597,557 | 1/1997 | Kumar et al. | 424/70.17 |
| 5,599,525 | 2/1997 | Hsu et al. | 424/53 |

*Primary Examiner*—Shep K. Rose
*Attorney, Agent, or Firm*—Henry S. Goldfine

[57] ABSTRACT

A striped dentifrice stable color bleeding, wherein at least one component contains a colorant entrained in the matrix of substantially non-fracturable, partially cross-linked melamine-urea-formaldehyde condensation polymer particles, whereby on storage the colorant does not bleed any color into any other dentifrice component. The dentifrice may also contain a formaldehyde scavenger to bind-up any formaldehyde released from the particles.

10 Claims, No Drawings

STRIPED DENTIFRICE STABLE TO COLOR BLEEDING

BACKGROUND OF THE INVENTION

1. Field of the Invention

This invention relates to aesthetically pleasing multicolored dentifrices and more particularly to a striped toothpaste or gel wherein there is virtually no colorant bleeding between the multicolored sections.

2. The Prior Art

Aesthetic effects have been acknowledged to play an important role in consumer acceptance of many products. In many cases ornamental effects have been used to distinguish particular products in the market place and to identify products having particular distinctive properties. In the dentifrice field, toothpastes and gels which have incorporated therein contrasting colored stripes are known. Such stripes provide an aesthetic effect which the user finds pleasing and promotes the use of the dentifrice, particularly by children.

A major problem impacting the aesthetic appearance of multicomponent striped toothpaste is the bleeding or migration of color from one component into another. This is especially severe if one colored component is applied to the surface of a white base. Also, in cases of thin surface striping, the concentration of the colorant added to the striping component(s) has to be very high, which can exacerbate bleeding. For this reason a colorant that exhibits no bleeding is required.

Striped dentifrice products containing water-soluble dyes are known in the prior art, for example as disclosed in U.S. Pat. Nos. 4,358,437, 4,568,534 and 4,487,757. A disadvantage to the use of water-soluble dyes enumerated in these patents is that they bleed in aqueous striped dentifrice formulations.

U.S. Pat. No. 4,814,160, discloses a two component striped dentifrice the particular chemical and physical properties of which inhibit bleeding of a limited group of dye colors, namely, beta-carotene (yellow) or chlorophyllin (green) gel and a white paste. The first component consists of these selected organic coloring agents in a translucent high water gel, having high concentrations of xanthan gum and the second component is a white paste containing a gelling agent limited to a mixture of lambda- and kappa carrageenans.

Dentifrice colorant alternatives to water-soluble dyes are pigments, which are essentially insoluble in water and do not exhibit the bleeding into aqueous dentifrice components encountered with dyes. Synthetic pigments such as phthalocanine have been used in a colored dentifrice stripe as disclosed in U.S. Pat. No. 4,456,585 and U.S. Pat. No. 4,518,578. However, such phthalocyanine pigments are disallowed for use in dentifrices in many countries around the world due to safety concerns.

U.S. Pat. Nos. 3,957,964, 3,929,988, 4,071,614 and 4,348,378 disclose the encapsulation or microencapsulation of flavors and other ingredients, to maintain such ingredients substantially separate from other dentifrice components and at least some of the dentifrice ingredients during manufacture and storage, while subsequently releasing such flavor or other ingredients into the dentifrice during normal use thereof. Use of such prior art encapsulating compositions to contain a dye has limitations, as for example, the encapsulating material may obscure the contained dye. As the disclosed encapsulating compositions are designed to fracture during the brushing process to release their contents, premature fracture is encountered during manufacture, packaging and/or extrusion from the package. Increasing the wall thickness of the encapsulating composition to reduce fracturing is not a viable alternative, as such an increase in material surrounding the dye will disadvantageously obscure its appearance, as well as deleteriously effect the mouthfeel of the dentifrice itself, while still not ensuring complete resistance to fracture.

U.S. Pat. Nos. 3,928,559, 4,007,259, 4,129,638 and 4,202,878 disclose the use of colored polymeric particles having a particle size of from about 150 to about 800 microns in size as dentifrice colorants. These relatively large sized particles disadvantageously alter the mouthfeel of the dentifrice and disadvantageously alter the uniform color appearance.

Accordingly, there is a need for a colorant composition useful in the striping of aqueous based dentifrices which will essentially eliminate colorant bleeding and which does not suffer from the other limitations and problems of the prior art.

SUMMARY OF THE INVENTION

In accordance with the present invention there is provided an aesthetically pleasing striped dentifrice, such as a paste or gel, containing a colorant entrained in the matrix of a clear, substantially non-fracturable, partially cross-linked melamine-urea-formaldehyde polymer, such as, polyoxymethylene-melamine-urea (hereinafter PMMU), the polymer being in the form of particles of from about 2 and about 70 microns in size, preferably from about 10 to about 30 microns in size. There may also be included in the dentifrice composition a scavenger compound to inactivate or bind-up any unreacted formaldehyde cross-linking agent which may separate out of the cross-linked melamine-urea-formaldehyde condensation polymer.

DESCRIPTION OF THE PREFERRED EMBODIMENTS

PMMU is identified by the CAS Registry Number 25036-13-9 (polymer) with the molecular formula $(C_3H_6N_6 \cdot CH_4N_2O \cdot CH_2O)_x$ and is available from many commercial sources under various trade names. Colored PMMU is available commercially from 3M Encapsulated Products Division of St. Paul, Minn., under the trade name of PMMU Colored Capsules.

The PMMU polymer in which the colorant is entrained, in accordance with the present invention, as measured by Coulter Counter has an average particle size in the range of from about 2 to about 70 microns, preferably from about 10 to about 30 microns, and most preferably from about 12 to about 16 microns; whereby, the particles are individually invisible, but, collectively provide a uniform colored appearance to the particular dentifrice component; are more resistant to fracture or breakage; and are small enough not to affect the mouthfeel of the dentifrice.

PMMU particles can be prepared by polycondensation techniques known to the art, as for example described in U.S. Pat. Nos. 3,516,941 and 4,201,404.

Colored PMMU particles can be prepared in an aqueous solution of the PMMU precondensate having a quantity of dissolved water-soluble dye sufficient to achieve the desired color intensity within the precondensate particles, the dye being from about 1 to about 10% by weight of the aqueous solution. An acid such as formic acid, acetic acid or citric acid is added to the solution in an amount sufficient to provide a pH within the aqueous solution in the range of about 1.5 to about 3.5, to catalyze the polymerization of the precondensate to a cross-linked melamine-urea-formaldehyde polymer, wherein the dye is entrained within the matrix of the water-insolubilized, PMMU polymer particles.

PMMU is stable within a pH range of from about 4.0 to about 10.0. Accordingly, the pH of the dentifrice component containing the colored PMMU particles is advantageously in the pH range of from about 6.0 to about 9.0.

Physiologically compatible water-soluble dyes suitable for entrainment in the PMMU matrix include natural or synthetic dyes of the types permitted in foods and drugs, such as those listed in Title 21 of the U.S. Code of Federal Regulations, section 74, including, for example, FD&C Blue #1 and FD&C Yellow #10.

In addition to these water-soluble dyes, it is also possible to use water-insoluble dyes, for example, Eyeshadow Blue KO, Colour Index 77 510, EG-No., Blue 15 (C-Blue 17), or even mixtures of water-insoluble dyes and water-soluble dyes, for example Eyeshadow Blue KO with Lemon Yellow ZN 3, in which case green hues are obtained.

To insure against trace amounts of unreacted formaldehyde being released into the dentifrice from the PMMU particles during aging or storage, a scavenger compound that acts to suppress or bind-up any released formaldehyde may be included in the dentifrice. Illustrative examples of scavenger compounds useful in the practice of the present invention include compounds such as, urea, alcohols, casein and sodium bisulfite. Casein, being a milk protein, is preferred. Scavenger compounds, when present in the dentifrice at concentrations of about 0.05 to about 5.0% by weight, are effective to reduce the level of free formaldehyde in PMMU containing dentifrices to undetectable levels at both ambient and elevated temperatures over prolonged periods of storage.

Sustained release of the scavenger compound may be achieved by microencapsulation of the formaldehyde scavenger in a polymer shell, formed of such materials as polyglycolic acid, polylactic acid, copolymers of polyglycolic acid and polylactic acid, gelatin or collagen.

In the preparation of a dentifrice composition in accordance with the present invention there is utilized an orally acceptable vehicle, including a water-phase with humectant, which is preferably glycerine or sorbitol, or an alkylene glycol such as polyethylene glycol or propylene glycol, wherein the water is present typically in an amount of about 3 to about 50% by weight, more typically about 5 to about 20%, and the glycerine, sorbitol and/or the alkylene glycol ingredients typically total about 15 to about 70% by weight of the dentifrice, more typically about 25 to about 50%.

Abrasive compounds may be present in the dentifrice and include sodium metaphosphate, potassium metaphosphate, tricalcium phosphate, dihydrated dicalcium phosphate, calcium carbonate, aluminum silicate, hydrated alumina, sodium bicarbonate, and calcined alumina. Preferred abrasives include dicalcium phosphate and siliceous materials, such as silica, and more preferably a precipitated amorphous hydrated silica, such as Zeodent 115, marketed by Huber Corporation. The abrasive is generally present in the dentifrice composition of the present invention in weight concentrations of about 10 to about 60%.

Suitable thickeners or gelling agents present in the dentifrice of the instant invention are natural or synthetic materials include Irish moss, iota-carrageenan, gum tragacanth, starch, polyvinylpyrrolidone, hydroxyethylpropyl-cellulose, hydroxybutyl methyl cellulose, hydroxypropyl methyl cellulose, hydroxyethyl cellulose and sodium carboxymethyl cellulose. Especially useful in the practice of the present invention are thickening silicas, such as Zeodent 165, marketed by Huber Corporation, and Sylox 15, available from W. R. Grace Corporation. Such a thickener or gelling agent is present in the dentifrice composition in proportions of about 0.1 to about 10% by weight, preferably about 0.5 to about 2% by weight.

Surfactants are used in the compositions of the present invention to achieve increased prophylactic action and render the dentifrice compositions more cosmetically acceptable. The surfactant is preferably a detersive material which imparts to the composition detersive and foaming properties. Suitable examples of surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, sodium lauryl sulfoacetate, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine.

The surfactant is typically present in the dentifrice compositions of the present invention in an amount of about 0.3 to about 5% by weight, preferably about 0.5 to about 2% by weight.

The dentifrice composition of the present invention may also contain a source of fluoride ions or fluorine-providing component, as anticaries agent in amount sufficient to supply about 25 ppm to 5,000 ppm of fluoride ions and include inorganic fluoride salts, such as soluble alkali metal, alkaline earth metal salts, for example, sodium fluoride, potassium fluoride, ammonium fluoride, sodium monofluorophosphate, stannous fluoride and sodium monofluoro-phosphate are preferred.

In addition to fluoride compounds, there may also be included antitartar agents such as pyrophosphate salts including dialkali or tetra alkali metal pyrophosphate salts such as $Na_4P_2O_7$, $K_4P_2O_7$, $Na_4K_2P_2O_7$, $Na_4H_2P_2O_7$ and $K_2H_2P_2O_7$ long chain polyphosphates such as sodium hexametaphosphate and cyclic phosphates such as sodium trimetaphosphate which are included in the dentifrice composition at a concentration of about 1 to about 5% by weight.

Synthetic anionic polymeric polycarboxylates may also be used in the dentifrice compositions of the present invention. Such anionic polymer polycarboxylates are generally employed in the form of their free acids or preferably partially or more preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000 most preferably about 30,000 to about 500,000. These copolymers are available, for example, as Gantrez, e.g. AN 139 (M.W. 500,000), AN 119 (M.W. 250,000); and preferably S-97 Pharmaceutical Grade (M.W. 70,000) of GAF Corporation.

The dentifrice composition of the present invention may also contain a flavoring agent. The flavoring agent is incorporated in the dentifrice composition at a concentration of about 0.1 to about 5% by weight and preferably about 0.5 to about 1.5% by weight.

Flavoring agents which are used in the practice of the present invention include essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Of these, the most commonly employed are the oils of peppermint and spearmint.

Various other materials may be incorporated in the dentifrice compositions of this invention, including antibacterial agents such as Triclosan, chlorhexidene, desensitizers such as potassium nitrate, whitening agents such as hydrogen peroxide, calcium peroxide and urea peroxide, preservatives, silicones, and chlorophyll compounds. These adjuvants, when present, are incorporated in the dentifrice composition in amounts which do not substantially adversely affect the properties and characteristics desired.

The preparation of dentifrices is well known in the art. U.S. Pat. Nos. 3,996,863, 3,980,767, 4,328,205 and 4,358,437, which are incorporated herein by reference, describe toothpastes and methods of production thereof which may be utilized for production of the dentifrices according to the present invention.

Dentifrice striping can be accomplished by either of the two techniques common in the art, namely surface striping and deep striping. Surface striping is created by a special nozzle through which the dentifrice is extruded from a tube or pump dispenser, wherein a separate reservoir of stripe material is positioned so that the initial deposition of the stripe on the base dentifrice segment is during extrusion. In deep striping systems by contrast, the layers of striping and base material are juxtapositioned in the dispenser in the pattern of the desired stripes, hence the initial deposition of the stripe on the base dentifrice is prior to extrusion from the dispenser. With surface striping, the quantity of striping material to base material in surface striping is generally in the ratio of about 5:95 to about 20:80; whereas, in deep striping the range can extend from about 10:90 to about 50:50. U.S. patents which further exemplify such striping methods include U.S. Pat. Nos. 4,969,767, 3,135,428, 2,914,220, 2,905,364, 2,873,887 and 2,789,731.

The following examples are illustrative of the subject invention, and do not limit it. All parts or percentages are by weight and all temperatures are in degrees C, unless specifically stated to be otherwise.

EXAMPLE I

A blue striped antibacterial toothpaste was prepared by a conventional deep striping procedure as previously described in accordance with the subject invention. The formulation being composed of two components, the first being a blue striping component and the second an opaque white base, the ingredients for both components are listed as follows.

| Ingredient | Weight Percent |
|---|---|
| Component A | |
| Opaque White Base | |
| Glycerine | 20.0 |
| Sodium Carboxymethylcellulose | 0.8 |
| Iota Carrageenan | 0.3 |
| Sodium Saccharin | 0.3 |
| Sodium Fluoride | 0.243 |
| Titanium Dioxide | 1.0 |
| Sorbitol | 19.5 |
| Deionized Water, irradiated | 16.857 |
| Gantrez | 15.0 |
| Sodium Hydroxide (50% solution) | 1.2 |
| Sodium Lauryl Sulfate (dental grade) | 1.5 |
| Zeodent 115 | 20.0 |
| Sylox 15 | 2.0 |
| Flavor (essential oil mixtures plus other components) | 1.0 |
| Triclosan | 0.3 |
| Component B | |
| Blue Stripe | |
| Glycerine | 20.0% |
| Sodium Carboxymethylcellulose | 0.8 |
| Iota Carrageenan | 0.3 |
| Sodium Saccharin | 0.3 |
| Sodium Fluoride | 0.243 |
| Sorbitol | 19.5 |
| Deionized Water, irradiated | 17.257 |
| FD&C Blue #1 Colored PMMU Particles | 0.5 |
| Casein | 0.1 |
| Gantrez | 15.0 |
| Sodium Hydroxide (50% solution) | 1.2 |
| Sodium Lauryl Sulfate (dental grade) | 1.5 |
| Zeodent 115 | 20.0 |
| Sylox 15 | 2.0 |
| Flavor (essential oil mixtures plus other components) | 1.0 |
| Triclosan | 0.3 |

A 50:50 proportion of component A was used with component B in the above blue striped antibacterial containing dentifrice.

Dye color bleeding in the striped dentifrice prepared in accordance with Example I, was determined after storage at 120° F., for 3 days, in a sealed plastic laminated tube using visible light spectroscopy to discern the concentration of dye having bled, or migrated, from the blue component into the white base component. The qualitative relationship of visible light spectrometric absorbance and dye concentration is determinable using Beer's Law:

$$A = elc$$

wherein: A is the maximum absorbance for each spectrometric measurement of a particular color dye (i.e. absorbance at $lamdba_{max}$ nm); e is the extinction coefficient, empirically established for the particular color dye, in units of $cm^{-1}M^{-1}$, wherein M is molarity or moles per liter; I is the length of the spectrometric sample cell, usually and in this case 1 cm; and c is concentration, in M.

Using a series of white base component samples with known concentrations of FD&C Blue #1 dye therein, the extinction coefficient, e, was established to be $1.28 \times 10^5$ $cm^{-1}M^{-1}$ for FD&C Blue #1 dye at a maximum blue absorbance occurring at 630 nm. Hence for FD&C Blue #1, knowing the extinction coefficient, e equal to $1.28 \times 10^5$ $cm^{-1}M^{-1}$; the spectrograph sample cell length, I equal to 1 cm; and establishing the maximum spectrometric absorbance, A, by spectrometric measurement at 630 nm of any dentifrice white base component subjected to FD&C #1

Blue dye bleeding, the concentration of FD&C #1 Blue dye that may have bled into the white base component can be calculated using Beer's Law.

It had been previously determined that FD&C Blue #1 in a dentifrice white base component was consumer perceivable if the concentration of the FD&C Blue #1 was about $5 \times 10^{-7}$ M, or greater.

The procedure used in obtaining the spectrometric absorbance, A, of a particular white base component sample for calculation of the concentration, c, of any dye was as follows: Apply a length, at least 4 inches, of the striped, two component dentifrice on a piece of paper. Using a 90 millimeter diameter, closed end capillary tube, remove a sample about 0.1 grams (g) of the dentifrice, about 0.1 to 0.2 inches into the white component, away from the colored stripe and dissolve the sample in about 1 milliliter of deionized water. Vigorously mix the sample to completely dissolve the white component and resolubilize the dye in the water phase. Centrifuge the sample for 2 to 3 minutes, separating the supernatant (containing the dissolved dye) and the solids of the white component. Measure with a Beckman Model DU-7 or similar spectrophotometer, the spectrometric absorbance, A, of the supernatant at the lambda$_{Max}$ and calculate the concentration, c, of the dye—equal to A divided by e times I (per Beer's Law).

The concentration of dye in the white base component A, in intimate contact with the FD&C Blue #1 striped component B, of the striped dentifrice of Example I, was determined by the above procedure and is recorded in Table I, below.

For purposes of comparison, the procedure of Example I was repeated to prepare a comparative striped dentifrice, designated Dentifrice C, except neither colored PMMU particles nor casein were present, instead 0.5% of free FD&C Blue #1 dye and 0.1% additional water were used in their place. A control striped dentifrice, without any colorant or casein was prepared in accordance with Example I, designated Dentifrice C1. 0.6% by weight additional water was substituted for the colorant and casein. The concentration of dye, after aging of Dentifrices C and C1, is also recorded in Table I below.

TABLE I

| Dye Bleeding in Striped Dentifrice Formulations | |
|---|---|
| Striped Dentifrice | Concentration of Dye in White Component (in M) |
| Example I | $8.6 \times 10^{-8}$ |
| Dentifrice C | $2.5 \times 10^{-6}$ |
| Dentifrice C1 | $7.8 \times 10^{-9}$ |

Referring now to Table I, the concentration of blue dye in the white base component of Example I was determined to be $8.6 \times 10^{-8}$, indicating no consumer perceivable bleeding. In the case of comparative striped Dentifrice C, the blue dye concentration, in the white base component was found to be $2.5 \times 10^{-6}$, indicating consumer perceivable bleeding. In the case of control striped Dentifrice C1, the concentration of blue dye was $7.8 \times 10^{-9}$, indicating no consumer perceivable bleeding.

EXAMPLE II

A blue striped baking soda and peroxide containing dentifrice was prepared by a conventional deep striping procedure as previously described in accordance with Example I. This baking soda and peroxide dentifrice was composed of two components, the first being a blue striping component and the second an opaque white base component. The ingredients for both components are listed below:

| Ingredient | Weight Percent |
|---|---|
| Component #1 | |
| Opaque White Baking Soda & Peroxide Containing Base | |
| Glycerine | 26.0% |
| Sodium Carboxymethylcellulose | 0.2 |
| Carrageenan | 0.2 |
| Saccharin | 0.5 |
| Sodium Monofluorophosphate | 0.76 |
| Titanium Dioxide | 2.0 |
| Propylene Glycol | 12.89 |
| Sodium Hydroxide (50% solution) | 1.5 |
| Tetrasodium Pyrophosphate | 2.0 |
| Sodium Tripolyphosphate | 3.0 |
| Deionized Water, irradiated | 10.0 |
| Zeodent 115 | 20.0 |
| Zeodent 165 | 1.5 |
| Sodium Bicarbonate | 16.0 |
| Sodium Lauryl Sulfate (dental grade) | 1.5 |
| Flavor (essential oil mixtures plus other components) | 0.95 |
| Calcium Peroxide | 1.0 |
| Component #2 | |
| Blue Stripe | |
| Glycerine | 26.0% |
| Carboxymethylcellulose | 0.2 |
| Iota Carrageenan | 0.2 |
| Sodium Saccharin | 0.5 |
| Sodium Monofluorophosphate | 0.76 |
| Propylene Glycol | 14.89 |
| Deionized Water, irradiated | 9.4 |
| FD&C Blue #1 PMMU Particles | 0.5 |
| Casein | 0.1 |
| Tetrasodium Pyrophosphate | 2.0 |
| Sodium Hydroxide (50% solution) | 1.5 |
| Sodium Lauryl Sulfate (dental grade) | 1.5 |
| Zeodent 115 | 21.0 |
| Zeodent 165 | 1.5 |
| Sodium Tripolyphosphate | 3.0 |
| Sodium Bicarbonate | 16.0 |
| Flavor (essential oil mixtures plus other components) | 0.95 |

A 50:50 proportion of component #1 was used with component #2 in the blue striped baking soda and peroxide containing dentifrice.

The concentration of dye in the white base component #1, in intimate contact with the FD&C Blue #1 striped component #2, was determined by the procedure described in Example I and is recorded in Table II, below.

A series of comparative striped dentifrices was prepared using the blue striped baking soda and peroxide dentifrice formulation procedure of Example II. The procedure of Example II was repeated to prepare a comparative striped dentifrice, designated Dentifrice C2, except neither colored PMMU particles nor casein were present, instead 0.5% of free FD&C Blue #1 dye and 0.1% additional water were used in their place. A control, without any colorant or casein was prepared in accordance with Example II, designated Dentifrice C3. 0.6% by weight additional water was substituted for the colorant and casein. The concentration of dye, after aging of each comparative dentifrice at 120° F. for 3 days, is also shown in Table II, below.

TABLE II

Dye Bleeding in Striped Baking Soda and Peroxide Dentrifice Formulations

| Striped Dentrifice | Concentration of Dye in White Component (M) |
| --- | --- |
| Example II | $9.3 \times 10^{-8}$ |
| Dentifrice C2 | $1.3 \times 10^{-6}$ |
| Dentifrice C3 | $8.3 \times 10^{-9}$ |

Referring now to Table II, the concentration of blue dye in the white base component of Example II was $9.3 \times 10^8$, indicating no consumer perceivable bleeding. In the case of comparative striped dentifrice formulation C2, the blue dye concentration in the white base component was found to be $1.3 \times 10^{-6}$, indicating consumer perceivable bleeding. In the case of control striped dentifrice C3, the concentration of blue dye was $8.3 \times 10^{-9}$, indicating no consumer perceivable bleeding.

EXAMPLE III

To demonstrate the efficacy of formaldehyde scavengers, a series of comparative striped two component dentifrices were tested for the presence of formaldehyde. Each comparative dentifrice was prepared in the manner of Example I, omitting casein. Further, the first dentifrice, designated Dentifrice D, was formulated without colored PMMU having in its place an equal quantity of FD&C Blue #1 dye. The second dentifrice, designated Dentifrice E, was formulated with colored PMMU particles dried at 165° C. for 2 to 3 hours after the coloring and condensation polymerization of the PMMU resin. For each of the dentifrices of D, and E, four subvariants were created, the first subvariant having no formaldehyde scavenger and an equal quantity of deionized water in its place in the dentifrice; the second having 0.1% casein; the third 0.1% urea; and the fourth 0.1% sodium bisulfite. The dentifrices were stored in sealed plastic laminated tubes and aged (i.e. storage) at 120° F. for a two week period.

High pressure liquid chromatography (HPLC) was used to establish the concentration of formaldehyde in the comparative dentifrices. The HPLC testing used a standard ESA Coulochem II electrochemical detector and a $C_{18}$ Column, 15 cm. in length. The quantity of formaldehyde was determined using standard HPLC practices from the relative peak heights obtained versus known standards. The concentrations of formaldehyde observed just after formulation of each dentifrice and after aging for the two week period are presented in Table III, below.

compounds present in the comparative dentifrices were successful in all cases in reducing the formaldehyde present to non-detectable levels.

We claim:

1. A surface or deep, contrasting stripe dentifrice composition stable to color bleeding comprising a plurality of components, at least one component having a visible, water soluble, FD&C approved natural or synthetic dye colorant entrained in the matrix of a substantially non-fracturable, partially cross-linked melamine-urea-formaldehyde condensation polymer particles of from about 2 to about 70 microns in size, containing an abrasive compound other than the condensation polymer particles and containing a microencapsulated formaldehyde scavenger, whereby on storage no observable colorant bleeding into any other component is present.

2. A dentifrice composition according to claim 1 wherein the partially cross-linked melamine-urea-formaldehyde condensation polymer is polyoxymethylene-melamine-urea.

3. The dentifrice composition according to claim 1, wherein particles are in a size range of from about 10 to about 30 microns.

4. The dentifrice composition according to claim 1 wherein the colorant is a physiologically compatible water-soluble dye.

5. The dentifrice composition according to claim 1, wherein the formaldehyde scavenger is selected from urea, casein, and sodium bisulfite, condensation polymer particles, whereby on storage of the dentifrice no observable colorant bleeding into any other component is present.

6. A method of preparing a non-bleeding surface or deep, contrasting stripe dentifrice comprising extruding a plurality of components, providing in at least one component a visible, water soluble, FD&C approved natural or synthetic colorant entrained in the matrix of partially cross-linked melamine-urea-formaldehyde condensation polymer particles of from about 2 to about 70 microns in size, containing an abrasive compound other than the condensation polymer particles and containing a microencapsulated formaldehyde scavenger, whereby on storage of the dentifrice no observable colorant bleeding into any other component is present.

7. The method of claim 6, wherein the partially cross-linked melamine-urea formaldehyde condensation polymer is polyoxymethylene-melamine-urea.

8. The method of claim 6, wherein particles are in a size range of from about 10 to about 30 microns.

9. The method of claim 6, wherein the colorant is a physiologically compatible water-soluble dye.

10. The method of claim 6, wherein the formaldehyde scavenger is selected from urea, casein, and sodium bisulfite.

TABLE III

Formaldehyde Levels in PMMV Dentifrices Containing Scavengers

| | SCAVENGER | | | | | | | |
| --- | --- | --- | --- | --- | --- | --- | --- | --- |
| | None (ppm) | | Urea (ppm) | | Casein (ppm) | | Sodium Bisulfite (ppm) | |
| Dentrifice | Before Aging | After Aging | Before Aging | After Aging | Before Aging | After Aging | Before Aging | After Aging |
| D | 1.2 | 1.5 | ND* | ND | ND | ND | ND | ND |
| E | 1.2 | 1.5 | ND | ND | ND | ND | ND | ND |

*ND = No formaldehyde detected at the lowest detectable range of less than 1 ppm.

The data recorded in Table III indicates that the scavenger